United States Patent
Kimmig et al.

(10) Patent No.: US 11,813,061 B2
(45) Date of Patent: Nov. 14, 2023

(54) IMPLANTABLE ELECTRIC MULTI-POLE CONNECTION STRUCTURE

(71) Applicant: Neuroloop GmbH, Freiburg (DE)

(72) Inventors: Fabian Kimmig, Freiburg (DE); Tim Boretius, Freiburg (DE); Dennis Plachta, Vörstetten (DE)

(73) Assignee: NEUROLOOP GMBH, Freiburg (DE)

( * ) Notice: Subject to any disclaimer, the term of this patent is extended or adjusted under 35 U.S.C. 154(b) by 1022 days.

(21) Appl. No.: 16/461,962

(22) PCT Filed: Nov. 17, 2017

(86) PCT No.: PCT/EP2017/079593
§ 371 (c)(1),
(2) Date: May 17, 2019

(87) PCT Pub. No.: WO2018/091654
PCT Pub. Date: May 24, 2018

(65) Prior Publication Data
US 2019/0320921 A1   Oct. 24, 2019

(30) Foreign Application Priority Data
Nov. 18, 2016   (DE) .................... 10 2016 222 712.2

(51) Int. Cl.
*A61N 1/00*   (2006.01)
*A61B 5/24*   (2021.01)
(Continued)

(52) U.S. Cl.
CPC .............. *A61B 5/24* (2021.01); *A61N 1/0556* (2013.01); *A61N 1/36125* (2013.01); *A61N 1/3752* (2013.01); *A61B 2562/222* (2013.01)

(58) Field of Classification Search
None
See application file for complete search history.

(56) References Cited

U.S. PATENT DOCUMENTS 4,573,481 A * 3/1986 Bullara ................ A61N 1/0556
607/118
5,324,322 A * 6/1994 Grill, Jr. .................. A61N 1/05
600/375
(Continued)

FOREIGN PATENT DOCUMENTS

DE   102014014927 A1   4/2016
WO   WO-2013159136 A1 * 10/2013 .......... A61N 1/0556
WO   WO-2017197084 A2 * 11/2017 ............... A61N 1/05

OTHER PUBLICATIONS

International Search Report for PCT/EP2017/079593, dated Jun. 20, 2018; English translation submitted herewith (6 pgs.).

*Primary Examiner* — John R Downey
*Assistant Examiner* — Anant A Gupta
(74) *Attorney, Agent, or Firm* — Fitch, Even, Tabin & Flannery LLP

(57) ABSTRACT

The invention relates to an implantable electric multi-pole connection between an electric implant and an electric feed and discharge structure. The invention is characterised in that a flexible, film-like, electrically non-conductive, strip-shaped surface element is arranged between the implant and the feed and discharge structure. The surface element comprises at least one first surface, on which a number of electrodes n greater than of equal to two is arranged, which are respectively connected to the electric implant by means of electric connection conductors extending at least in parts inside the surface element. The electric feed and discharge structure comprises at least n lines which are electrically insulated from each other and which are electrically connected to one of the n electrodes. The strip-shaped surface element is wound around a winding axis, which adopts the shape of a helix, along a cover surface of a virtual cylinder provided with a cylinder axis which is straight or curved at least in sections.

18 Claims, 2 Drawing Sheets

(51) Int. Cl.
*A61N 1/05* (2006.01)
*A61N 1/36* (2006.01)
*A61N 1/375* (2006.01)

(56) References Cited

U.S. PATENT DOCUMENTS

| | | |
|---|---|---|
| 2008/0082137 A1 | 4/2008 | Kieval et al. |
| 2010/0192374 A1 | 8/2010 | Maschino et al. |
| 2011/0077699 A1 | 3/2011 | Swanson et al. |
| 2017/0319846 A1 | 11/2017 | Plachta et al. |
| 2018/0056074 A1* | 3/2018 | Clark .................. A61N 1/3787 |

* cited by examiner

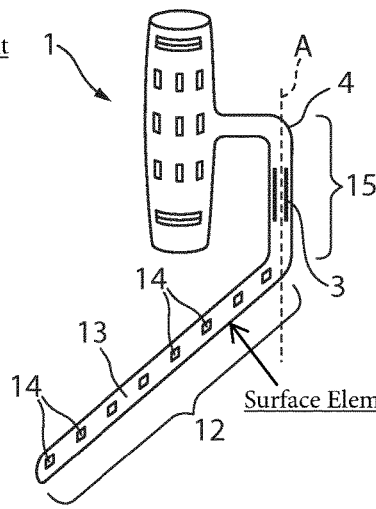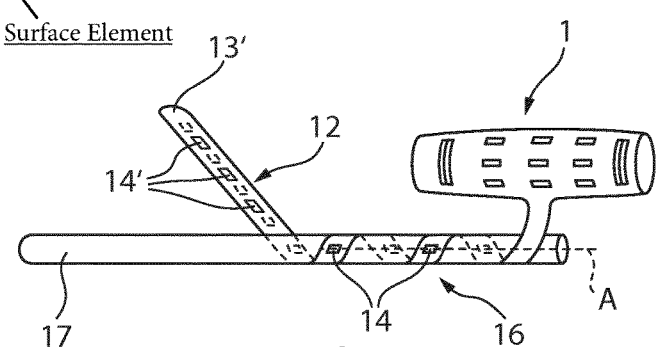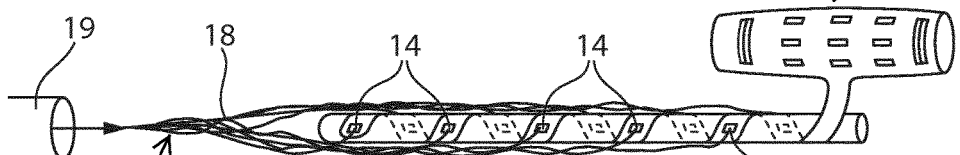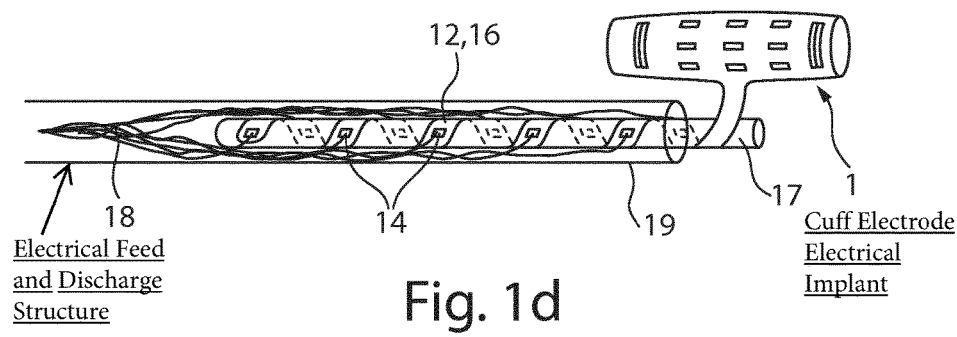

IMPLANTABLE ELECTRIC MULTI-POLE CONNECTION STRUCTURE

CROSS REFERENCE TO RELATED APPLICATIONS

Reference is made to PCT/EP2017/079593 filed Nov. 17, 2017, and German Application No. 10 2016 222 712.2 filed Nov. 18, 2016, which are incorporated herein by reference in their entirety.

BACKGROUND OF THE INVENTION

Field of the Invention

The invention relates to an implantable electric, multi-pole connection between an electric implant and an electric feed and discharge structure.

Description of the Prior Art

Electronic implants suitable for permanent or at least long-term retention in the body are typically used to influence organ functions therapeutically. Examples of known art are cardiac or brain pacemakers. Depending on the application purpose and complexity of the therapeutic objective, generic implants have a large number of electrical feed and discharge lines, which supply the implant in question with electrical control and regulatory signals as well as electrical power. The number of electrical feed and discharge lines for electronically complex implants may well include twenty or more electrical lines assembled into a flexible cable, by which the implant is connected to a control unit, which is usually combined with a power source. The intra-corporeal positioning of the control unit and the power source is usually performed subcutaneously in a part of the body, such as the chest region or near the clavicle, where the external and internal stresses caused by movement are as small as possible for the person, and ease of surgical access is possible.

As a rule, the electrical feed and discharge lines between the implant and the control unit or power source are not integratively designed, but are implemented via at least one interface in the form of an intra-corporeal plug connection, or a detachable or non-detachable electrical connection, such as a bonded or soldered connection. On the one hand, this raises problems related to the installation space required for the interface, and on the other hand it is necessary to make the interface region moisture-resistant on account of the moist intra-corporeal environment.

Using the example of an implantable cuff electrode arrangement to be supplied via a multi-pole feed and discharge structure, the problems existing up to the present time of an implantable electrical multi-pole connection structure known per se will be explained in more detail with reference to the illustrations to be found in FIGS. 2a and b.

Figure 2A:
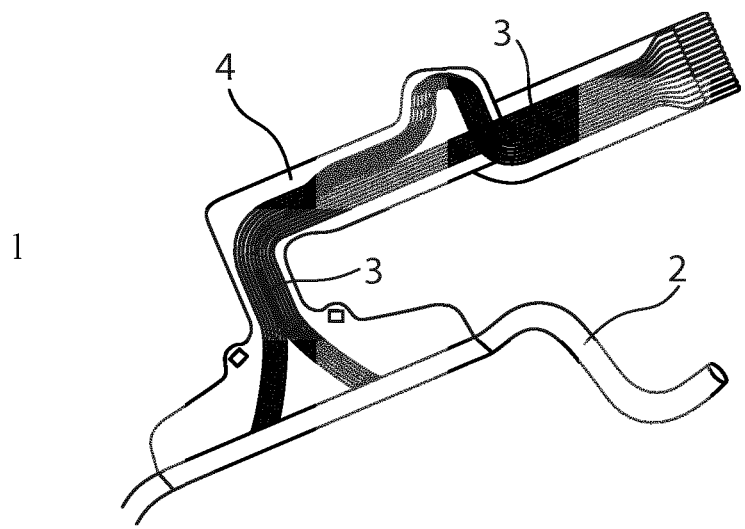

FIG. 2a shows a cuff electrode arrangement 1, which is designed as a winding electrode so as to surround a nerve fiber bundle 2. For the purpose of therapeutic stimulation of the nerve fiber bundle 2, the cuff electrode arrangement 1 provides a large number of individual electrode surfaces, which are supplied separately from each other with electrical power and control signals. For this purpose, the multiplicity of individual electrical feed and discharge lines 3 run inside a flexible, flat supporting substrate 4, which is formed as a polymer film. The electric feed and discharge lines 3 end in an end face connection structure of so-called electrically conductive microflex structures 5 arranged side by side, which are shown in detail in FIG. 2b and with which individual electrical contact must be made.

Figure 2B:
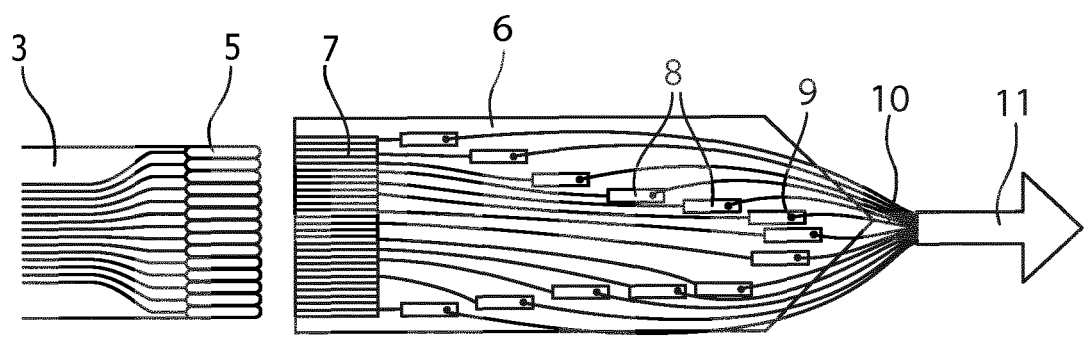

For the purpose of making electrical contact with the microflex structures 5, a ceramic adapter plate 6 is used in a manner known per se, on which, in accordance with the number and arrangement of the microflex structures 5, so-called microflex contacts or microflex pads 7 are attached; these are brought into contact with the microflex structures 5 and are in each case connected individually in an electrically conductive manner to the electrode surfaces 8 attached to the surface of the ceramic adapter plate 6. Individual electric wires 10 of an electric cable 11 are connected to the individual electrode surfaces 8 formed as solder pads via soldered or bonded connections 9. Needless to say, the entire electric connection arrangement shown in FIG. 2b is surrounded by a biocompatible plastic in as impermeable a manner as possible.

It is obvious that the installation space required for the electrical connection structure of known art increases with the increasing complexity and multi-polarity of the unit to be implanted, as a result of which patient stress and irritation also increases in the same manner.

U.S. Pat. No. 5,324,322 discloses an implantable electrode arrangement with a winding electrode component in a type of cuff electrode, which is connected via a connecting section to a multi-pole connection structure of planar design, onto which a number of electric contact surfaces are applied. In one example of an embodiment, the planar connection structure is wound around an axis, in a manner similar to the winding electrode component. In the wound state, the connection structure takes the form of a hollow cylinder, which has a rigid structure and for the purpose of intra-corporeal location is placed section-by-section around a nerve fiber strand.

SUMMARY OF THE INVENTION

The invention is a design of an implantable, electric, multi-pole connection structure between an electric implant and an electrical feed and discharge structure, for example in the form of a multi-pole cable, so that the stress on the patient is significantly reduced, compared to generic connection structures of known art, despite the large number of individual electrical feed lines with which contact is to be made on the implant side. The measures required for this should make it possible to connect an arbitrarily scalable number of electrical feed lines to an implant via a multi-pole connection structure, without requiring any appreciable additional installation space for this purpose.

The implantable electrical, multi-pole connection structure in accordance with the invention is a flexible, film-like, electrically non-conductive, strip-shaped surface element arranged between the implant and the feed and discharge structure, with at least a first surface of the surface element, on which a number of electrodes n≥2 is arranged. Each of the n electrodes is connected to an electrical connection conductor, which is connected to the electrical implant for purposes of at least one of signal control and power supply. The at least n electric connection conductors run at least in parts inside the surface element.

The electrical feed and discharge structure comprises at least n wires, electrically insulated from each other, which are electrically connected at their ends to one of the n electrodes, for example by way of a bonded or soldered connection. In addition, the strip-shaped surface element, along the at least first surface of which the n electrodes are arranged, and in each case are connected to one of the n wires, is wound around a winding axis, which adopts the shape of a helix, along a cover surface of a virtual cylinder provided with a cylinder axis, which is straight or curved at least in sections.

As a result of the winding of the strip-shaped surface element, in accordance with the invention, around a cylinder axis, which is straight or curved at least in sections, along which the electrical feed and discharge structure preferably extends in the form of a bundle of wires, which are assembled as a cable, no additional installation space is required other than that which is already required for the feed and discharge structure. By virtue of the flexibility of the film-like, electrically non-conductive surface element, the patient does not experience any appreciable irritating sensations, as would otherwise arise from a ceramic adapter plate made of rigid material. Instead, the multi-pole, elastic connection structure designed in accordance with the invention is able to adapt individually to the intra-corporeal spatial conditions in question.

A particularly preferred embodiment provides for an integrative design and connection of the implant with the flexible, film-like, electrically non-conductive surface element, in which the number of electric connection conductors n is completely enclosed and integrated, and the ends with which contact is to be made terminate in each case on an electrode on at least a first surface of the surface element. The integrative design of implant and surface element on the one hand makes an electrical contact arrangement between implant and electrical connection structure as the surface element superfluous, and on the other hand, an almost arbitrarily scalable number of electrical connection conductors and their contact electrodes can be implemented with a high degree of integration in the region of the surface element using microsystems process technology.

For reasons of a uniform and procedurally simplest possible feasibility of the electrical contacts between the electrodes provided on the upper surface of the surface element and the individual wires, electrically insulated from each other, of the electrical feed and discharge structure, in what follows is referred to simply as the cable, all n electrodes are arranged on a common surface of the surface element. This also has the additional advantage that after the surface element has been appropriately wound, all wires connected to the surface element are uniformly connected to the electrodes on the surface of the surface element either facing towards or away from the winding axis. The surface element is preferably wound in such a way that the surface of the surface element provided with electrodes is facing radially towards the winding axis or cylinder axis, so that the wires connected to the individual electrodes are radially surrounded at least in parts by the surface element in the wound state.

In order to provide as large a number of electrodes as possible on the surface element, one embodiment envisages populating both opposing surfaces of the surface element with a corresponding number of electrodes, which in each case are connected to the electrical implant via an electrical connection conductor running at least in parts inside the surface element. The number of electrodes n on the first surface of the surface element does not necessarily have to correspond to the number of electrodes m on the opposing second surface of the surface element.

The electrical connection of the individual wires of the cable to the respective electrodes on the at least first surface of the surface element is preferably made by soldering, welding or bonding.

In order to protect the electrical contacts on the electrodes along the wound surface element, together with the wires leading away from the individual electrodes, from the moist intra-corporeal environment, a preferred embodiment provides for a sheath of an electrically insulating, biocompatible material, which preferably fully surrounds at least the region of the surface element. The sheath can be in the form of a tubular potting compound, or in the form of an impermeable shrinkable tube. A person skilled in the art has all the known potting and sheathing techniques necessary to meet all medical product-specific requirements.

The strip-shaped design of the surface element, that is the fact that the surface element is characterised by a longitudinal extent that is much larger than the width that can be assigned to the surface element, enables a helical winding of the strip-shaped surface element along a cover surface of a virtual cylinder. By virtue of the helical winding shape, the strip-shaped surface element in the wound state has a high deformability, or elasticity, transverse to the winding axis, so that a spatial shape of the connection structure is enabled that can be adapted at will to the individual spatial, intra-corporeal conditions, whereby patient stress can also be minimized, in particular in cases in which the connection structure has a large number of electrical contacts. The large number of electrodes n are preferably arranged along the upper surface of the strip oriented radially inwards. In this manner, the numerous n wires leading away from the individual electrodes are radially surrounded by the spiral or helical, strip-shaped surface element.

In order to prevent the electrical contact points of all wires from forming electrical short-circuits with each other after the surface element has been appropriately wound, the contact points are accordingly mutually insulated with a potting compound or an additional coating. In a preferred embodiment, the cylindrical volume, which surrounds the surface element wound around the winding axis and located radially inside, is filled with an elastic, electrically insulating, biocompatible material.

The compliant multi-pole connection structure of the invention, in the form of the flexible, film-like, electrically non-conductive surface element, is not necessarily possible to be connected to the implant. It is also possible that only the electric connection conductors running at least in parts inside the surface element are connected directly or indirectly to the implant and lead into the surface element that is separate from the implant.

The invention's compliant implantable electric multi-pole connection structure is particularly suitable for electrical signal and power transmission between an implant designed as a cuff electrode arrangement and an intra- or extra-corporeal electrical control and power unit.

A cuff electrode arrangement known per se has already been described with reference to FIGS. 2a and 2b, and is used in a manner known per se for the location-selective acquisition of neuronal electric signals, which propagate along at least one nerve fiber contained in a nerve fiber bundle, and also for the selective electrical stimulation of the at least one nerve fiber. The cuff electrode arrangement known per se provides for a biocompatible supporting substrate which has at least one supporting substrate region, which can be placed around the nerve fiber bundle in the form of a cuff, and in the implanted state has a straight cylindrical supporting substrate surface which is oriented towards the nerve fiber bundle, to which a number of electrodes n is attached, each of which is connected via electrical lines running inside the biocompatible supporting substrate. The compliant surface element is integratively connected to the biocompatible supporting substrate of the invention, so that the electrical lines inside the supporting substrate lead seamlessly into the region of the surface element, where they are connected to the n electrodes on the surface of the surface element.

The integrative design of the supporting substrate with the invention's compliant design of the surface element is particularly suitable, because both the supporting substrate and the surface element are of a film-like design and are a flexible, electrically non-conductive material, which preferably is a polymer and most preferably a polyimide. In the same way as the supporting substrate region, which lies in a cuff around the nerve fiber bundle, and which is able to wind or roll itself up by an implantation of a mechanical pre-stress by use of process and material; the surface element, which has the n-electrodes and is preferably a strip, is also embodied with a mechanical pre-stress for the purpose of an independent winding. Further details on the compliant implantable electric multi-pole connection structure of the invention can be found with reference to the following figures.

BRIEF DESCRIPTION OF THE INVENTION

The invention will be described below in an exemplary manner by way of embodiments with reference to the figures, without any limitation of the general inventive concept. Here:

FIGS. 1a to d illustrate a compliant design of cuff electrode arrangement of the invention, in the form of a sequence of images for the design of the same, and FIGS. 2a, and b show a prior art implantable connection structure.

DETAILED DESCRIPTION OF THE INVENTION

FIG. 1a illustrates a compliant design of cuff electrode arrangement 1, which is integratively connected to a strip-shaped surface element 12. The surface element 12 and the supporting substrate 4 of the cuff electrode arrangement 1 are made of a uniform material, preferably a polyimide, and represent a flexible, electrically non-conductive film. Electrical lines 3 run inside the supporting substrate 4 in a manner known per se, and are connected on the one hand to electrodes of the cuff electrode arrangement 1, and on the other hand to electrodes 14 that are attached to the surface 13 of the strip-shaped surface element 12 and are in the form of soldering or bonding pads. For this purpose, the electrical lines run embedded inside the supporting substrate 4 and along the strip-shaped surface element 12.

The supporting substrate 4 has an elongated supporting substrate section 15, which extends along an axis A. The axis A defines the winding axis around which the strip-shaped surface element 12 is wound, forming a helical wound structure.

FIG. 1b illustrates the winding process, in accordance with which the strip-shaped surface element 12 is wound around the winding axis A, thereby forming a helix 16. Optionally, an auxiliary cylindrical body 17 can be used for the winding process, which can be removed after completion of the winding process, or left as an electrically insulating body. In this case, the auxiliary body 17 is preferably made of an elastic, electrically non-conductive, biocompatible material.

Before or after the winding process, the individual electrodes 14, which are distributed along the strip-shaped surface element 12, are connected to the ends of electrical wires 18, for example by way of a soldering or bonding process. See FIG. 1c. All the wires 18 are assembled to form a compact, flexible cable. This can be done, for example, by sliding a sheath 19 lengthwise onto the formed helix 16. The sheath 19 is a biocompatible electrically insulating material, for example in the form of a swollen silicon tube.

After appropriate shrinking of the silicon tube and, if necessary, additional internal filling of the tube volume with a suitable material, preferably PDMS, an impermeable protection of all internal electrical contact surfaces is achieved, see FIG. 1d.

In contrast to the connection technique of known art described above, the compliant implantable electrical multi-pole connection structure has a high degree of flexibility and requires only one single electrical connection per wire, which can be produced by way of a bonding, welding or soldering process. Furthermore, the number of electrodes and thus the multi-polarity of the connection structure can be scaled to almost any extent. Thus, in this context, the strip-shaped surface element 12 can be appropriately extended on the one hand, and populated with electrodes on both surfaces of the surface element on the other hand, that is in addition to the n electrodes 14 on the first surface 13 of the surface element, a number of electrodes (14') m, greater than or equal to two, are attached to a second surface (13') of the surface element, which is oriented away from the first surface (13) of the surface element. See FIG. 1b.

LIST OF REFERENCE SYMBOLS

1 Cuff electrode arrangement
2 Nerve fibre bundle
3 Electric lines
4 Biocompatible supporting substrate
5 Microflex structures
6 Ceramic adaptor plate
7 Microflex contacts, microflex pads
8 Electrode surfaces
9 Solder point
10 Electric supply wire
11 Cable
12 Strip-shaped surface element
13 First surface of the surface element
13' Second surface of the surface element
14, 14' Electrode
15 Supporting substrate section
16 Helix
17 Auxiliary body
18 Wires
19 Sheath
A Winding axis

The invention claimed is:

1. An implantable electrical multi-pole connection configured for implantation which is electrically connected when implanted between an electrical implant and an electrical feed and discharge implant, the implantable electrical multi-pole connection comprising:
  a flexible electrically non-conductive strip-shaped surface element configured for connecting the electrical implant to the electrical feed and discharge implant having at least one surface on which at least two electrodes are located which are electrically connected when implanted to the electrical implant by electrical conductors running at least partially inside the flexible electrically non-conductive strip-shaped surface element; and wherein the electrical feed and discharge structure comprises electrically insulated wires with each wire being electrically connected to a different one of the electrodes; and the flexible electrically non-conductive surface element is wound into a helical winding providing a cover surface of a virtual cylinder which is straight or curved at least in sections when the implantable electrical multi-pole connection is connected when implanted between the electrical implant and the electrical feed and discharge implant.

2. The implantable electrical multi-pole connection in accordance with claim 1, wherein the at least one surface of the surface element either radially faces towards or away from the cover surface of the virtual cylinder surface.

3. The implantable electrical multi-pole connection in accordance with claim 1, wherein:

the flexible electrically non-conductive surface element has a second surface along which are located electrodes with each electrode of the second surface being connected to the electrical implant via the electrical conductors running at least partially inside the non-conductive surface element; and the second surface element faces away from the first surface of the surface element.

4. The implantable electrical multi-pole connection in accordance with claim 1, comprising:

a tubular sheath including an electrically insulating biocompatible material and the electrical conductors connected to the electrodes are positioned around the flexible electrically non-conductive surface element.

5. The implantable electrical multi-pole connection in accordance with claim 1, wherein the flexible electrically non-conductive surface element comprises a cylinder filled with an elastic electrically insulating biocompatible material.

6. The implantable electrical multi-pole connection in accordance with claim 1, wherein the electrical implant and the flexible electrically non-conductive surface element are integrated together.

7. The implantable electrical multi-pole connection in accordance with claim 2, wherein the electrical implant and the flexible electrically non-conductive surface element are integrated together.

8. The implantable electrical multi-pole connection in accordance with claim 3, wherein the electrical implant and the flexible electrically non-conductive surface element are integrated together.

9. The implantable electrical multi-pole connection in accordance with claim 4, wherein the electrical implant and the flexible electrically non-conductive surface element are integrated together.

10. The implantable electrical multi-pole connection in accordance with claim 5, wherein the electrical implant and the flexible electrically non-conductive surface element are integrated together.

11. The implantable electrical multi-pole connection in accordance with claim 1, wherein electrical signal and power transmission are provided by the implantable multi-pole connection when implanted between the electrical implant configured as a cuff electrode and an electrical control and power unit.

12. The implantable electrical multi-pole connection in accordance with claim 2, wherein an electrical signal and power transmission are provided by the implantable multi-pole connection when implanted between the electrical implant configured as a cuff electrode and an electrical control and power unit.

13. The implantable electrical multi-pole connection in accordance with claim 3, wherein an electrical signal and power transmission are provided by the implantable multi-pole connection when implanted between the electrical implant configured as a cuff electrode and an electrical control and power unit.

14. The implantable electrical multi-pole connection in accordance with claim 4, wherein the electrical feed and discharge implant comprises means for providing electrical signal and power transmission.

15. The implantable electrical multi-pole connection in accordance with claim 5, wherein electrical signal and power transmission are provided by the implantable multi-pole connection when implanted between the electrical implant configured as a cuff electrode and an electrical control and power unit.

16. The implantable electrical multi-pole connection in accordance with claim 6, wherein an electrical signal and power transmission are provided by the implantable multi-pole connection when implanted between the electrical implant configured as a cuff electrode and an electrical control and power unit.

17. The implantable electrical multi-pole connection in accordance with claim 11, wherein the cuff electrode records location-selective neuronal electrical signals propagating along at least one nerve fiber contained in nerve fiber bundle for providing selective electrical stimulation of the at least one nerve fiber when implanted.

18. The implantable electrical multi-pole connection in accordance with claim 17, wherein when implanted the non-conductive surface element comprises polyimide.

* * * * *